(12) United States Patent
Bowles et al.

(10) Patent No.: US 11,299,500 B2
(45) Date of Patent: Apr. 12, 2022

(54) CRYSTALLINE FORM OF LORLATINIB FREE BASE HYDRATE

(71) Applicant: Pfizer Inc., New York, NY (US)

(72) Inventors: Paul Bowles, Ledyard, CT (US); Peter Robert Rose, Uncasville, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 16/650,505

(22) PCT Filed: Oct. 4, 2018

(86) PCT No.: PCT/IB2018/057735
§ 371 (c)(1),
(2) Date: Mar. 25, 2020

(87) PCT Pub. No.: WO2019/073347
PCT Pub. Date: Apr. 18, 2019

(65) Prior Publication Data
US 2020/0308191 A1     Oct. 1, 2020

Related U.S. Application Data

(60) Provisional application No. 62/727,734, filed on Sep. 6, 2018, provisional application No. 62/570,326, filed on Oct. 10, 2017.

(51) Int. Cl.
| *C07D 498/18* | (2006.01) |
| *A61P 35/00* | (2006.01) |
| *A61K 31/439* | (2006.01) |

(52) U.S. Cl.
CPC ........ *C07D 498/18* (2013.01); *C07B 2200/13* (2013.01)

(58) Field of Classification Search
CPC ............... C07D 498/18; C07B 2200/13; A61P 35/00; A61K 31/439
See application file for complete search history.

(56) References Cited

U.S. PATENT DOCUMENTS

| 8,680,111 | B2 | 3/2014 | Bailey et al. |
| 9,133,215 | B2 | 9/2015 | Bailey et al. |

FOREIGN PATENT DOCUMENTS

| WO | 2011/138751 A2 | 11/2011 |
| WO | 2012121764 | 9/2012 |
| WO | 2012170923 | 12/2012 |
| WO | 2013/132376 A1 | 9/2013 |
| WO | 2014/207606 A1 | 12/2014 |
| WO | 2017/021823 A1 | 2/2017 |
| WO | 2017/175091 A1 | 10/2017 |

OTHER PUBLICATIONS

Syed, Y. Y. ,"Lorlatinib: first global approval." Drugs 79.1 (2019): 93-98.*
Hwang, J., "KRCA-0008 suppresses ALK-positive anaplastic large-cell lymphoma growth." Investigational new drugs (2020) 38: 1282-1291.*
Pastor, E. R., "Current management of neuroblastoma and future direction." Critical reviews in oncology/hematology 138 (2019): 38-43.*
Gadgeel, Shirish M. "Sequencing of ALK inhibitors in ALK+ non-small cell lung cancer." Current treatment options in oncology 18.6 (2017) 36: 1-12.*
Sakamoto, H., "CH5424802, a selective ALK inhibitor capable of blocking the resistant gatekeeper mutant." Cancer cell 19.5 (2011): 679-690.*
Awad, M., et al., "Acquired Resistance to Crizotinib from a Mutation in CD74-ROS1", N Engl J Med, 2013; 368:2395-2401.
Bergethon, K., et al., "ROS1 rearrangements define a unique molecular class of lung cancers", J Clin Oncol, 2012; 30(8): 863-70.
Byrn, S., et al., "Pharmaceutical Solids: A Strategic Approach to Regulatory Considerations", Pharmaceutical Research, 1995; 12(7): 945-954.
Gainor, J., et al., "Molecular Mechanisms of Resistance to First- and Second-Generation ALK Inhibitors in ALK-Rearranged Lung Cancer", Cancer Discov., 2016; 6(10): 1118-33.
International Search Report for PCT/IB2018/057735, dated Nov. 20, 2018 and dated Dec. 4, 2018.
Johnson, T., et al., "Discovery of (10/R)-7-Amino-12-fluoro-2,10,16-trimethyl-15-oxo-10,15,16,17-tetrahydro-2H-8,4-(metheno)pyrazolo[4,3-h][2,5,11]-benzoxadiazacyclotetradecine-3-carbonitrile (PF-06463922), a Macrocyclic Inhibitor of Anaplastic Lymphoma Kinase (ALK) and c-ros Oncogene 1 (ROS1) with Preclinical Brain Exposure and Broad-Spectrum Potency against ALK Resistant Mutations", J. Med. Chem., 2014; 57, 4720-4744.
Rikova, K., et al., "Global survey of phosphotyrosine signaling identifies oncogenic kinases in lung cancer", Cell, 2007; 131:1190-1203.
Soda, et al., "Identification of the transforming EML4-ALK fusion gene in non-small cell lung cancer", Nature, 2007 148:561-566.
WHO Drug Information, vol. 29, No. 4, p. 541 (2015).
Written Opinion for PCT/IB2018/057733, dated Nov. 20, 2018 and dated Dec. 4, 2018.
Bavin, Mike, "Polymorphism in Process Development", Chemistry & Industry 1989 pp. 527-529.
Caira, M., "Crystalline Polymorphism of Organic Compounds", Topics of Current Chemistry, 1998, vol. 198 p. 163-208.
Day, G., "Investigating the latent polymorphism of maleic acid", Chem. Comm., 2006, 54-56.
Desiraju, G.R., A method for predicting crystal structures from just molecular formulae has eluded scientists for more than 50 years. The problem is currently being addressed by two very different approaches. But which one is more likely to succeed?, Nature Materials, 2002, 1, 77-79.
Gadgeel, S., "Sequencing of ALK Inhibitors in ALK+ Non-Small Cell Lung Cancer", Current Treatment Options in Oncology 2017 18(36):1-12.

(Continued)

Primary Examiner — John M Mauro
(74) Attorney, Agent, or Firm — Fariba Shoarinejad (57) ABSTRACT

This invention relates to a crystalline form of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclo-tetradecine-3-carbonitrile (lorlatinib) free base hydrate (Form 24). This invention also relates to pharmaceutical compositions comprising Form 24, and to methods of using Form 24 and such compositions in the treatment of abnormal cell growth, such as cancer, in a mammal.

13 Claims, 6 Drawing Sheets

(56) References Cited

OTHER PUBLICATIONS

Hwang, J., et al., "KRCA-0008 suppresses ALK-positive anaplastic large cell lymphoma growth", Investigational New Drugs 2020 38:1282-1291.

Pastor, E., et al. "Current management of neuroblastoma and future direction", Critical Reviews in Oncology/Hematology 2019 138:38-43.

Pirttimaki, J., et al., "Effect of grinding and compression on crystal structure of anhydrous caffeine", Int. Journal of Pharmaceutics, 1993, pp. 93-99.

Sakamoto, H., et al., "CH5424802, a Selective ALK Inhibitor Capable of Blocking the Resistant Gatekeeper Mutant", Cancer Cell, 2011, 19, 679-690.

Sherry L. Morissette et al., "High-throughput crystallization: polymorphs, salts, co-crystals and solvates of pharmaceutical solids", Advanced Drug Delivery Reviews, 2004, v. 56, pp. 275-300 (section 1; 3.1).

Suryanarayanan, Raj, "Determination of the Relative Amounts of α-carbazepine and β-carbazepine in a Mixture by Powder X-Ray Diffractometry", Dept. of Pharmaceutics, U. Minnesota, 1990, vol. 5, No. 3 pp. 155-159.

Syed, Yahiya Y., "Lorlatinib: First Global Approval", Drugs, 2019, 79:92-98.

\* cited by examiner

13C Chemical Shift (ppm)

FIG. 3

19F Chemical Shift (ppm)

19F Chemical Shift (ppm)

CRYSTALLINE FORM OF LORLATINIB FREE BASE HYDRATE

CROSS-REFERENCE TO RELATED APPLICATIONS

This Application is the national stage filing under 35 U.S.C. 371 of Patent Cooperation Treaty Patent Application No. PCT/IB2018/057735, filed Oct. 4, 2018, which claims the benefit of priority from U.S. Provisional Application No. 62/570,326 filed Oct. 10, 2017, and U.S. Provisional Application No. 62/727,734 filed Sep. 6, 2018, the contents of each of which are hereby incorporated by reference in their entirety.

BACKGROUND OF THE INVENTION

Field of the Invention

This invention relates to a new crystalline form of (10R)-7-amino-12-fluoro-2,10,16-trimethyl-15-oxo-10,15,16,17-tetrahydro-2H-8,4-(metheno)pyrazolo[4,3-h][2,5,11]benzoxadiaza-cyclotetradecine-3-carbonitrile (lorlatinib) free base hydrate (Form 24), to pharmaceutical compositions comprising Form 24, and to methods of using Form 24 and such compositions in the treatment of abnormal cell growth, such as cancer, in mammals.

Description of the Related Art

The compound (10R)-7-amino-12-fluoro-2,10,16-trimethyl-15-oxo-10,15,16,17-tetra-hydro-2H-8,4-(metheno)pyrazolo[4,3-h][2,5,11]benzoxadiazacyclotetradecine-3-carbonitrile (PF-06463922), represented by the formula (I):

(I)

has been assigned the International Nonproprietary Name (INN) lorlatinib, as described in *WHO Drug Information*, Vol. 29, No. 4, page 541 (2015). Lorlatinib is a potent, macrocyclic inhibitor of anaplastic lymphoma kinase (ALK) and c-ros oncogene 1 (ROS1) receptor tyrosine kinase. Lorlatinib demonstrates nanomolar potency against both wild type and resistance mutant forms of ALK and ROS1, including ALK G1202R and ROS1 G2032R. It was designed to penetrate the blood-brain barrier and has demonstrated antitumor activity in ALK-positive NSCLC xenograft models and intracranial ALK-positive tumor models.

Preparation of the free base of lorlatinib as an amorphous solid is disclosed in International Patent Publication No. WO 2013/132376 and U.S. Pat. No. 8,680,111. Preparation of an acetic acid solvate and two hydrated forms of lorlatinib free base is disclosed in International Patent Publication No. WO 2014/207606. Preparation of an anhydrous crystalline free base (Form 7) of lorlatinib is disclosed in International Patent Publication No. 2017/021823. Preparation of a crystalline maleate salt of lorlatinib is disclosed in International Patent Publication No. WO 2017/175091. The contents of each of the foregoing documents are incorporated herein by reference in their entirety.

Chromosomal rearrangements of ALK and ROS1 define distinct molecular subtypes of non-small cell lung cancer (NSCLC), accounting for an estimated 2-7% and 1-3% of NSCLC cases, respectively. (Soda et al., Identification of the transforming EML4-ALK fusion gene in non-small cell lung cancer, Nature 2007; 448:561-566; Rikova et al., Global survey of phosphotyrosine signaling identifies oncogenic kinases in lung cancer, Cell 2007; 131:1190-1203; Bergethon et al., ROS1 rearrangements define a unique molecular class of lung cancers, J Clin Oncol. 2012; 30 (8): 863-70).

The ALK/ROS1/c-MET inhibitor crizotinib is the standard first-line therapy for patients with advanced or metastatic ALK- or ROS1-positive NSCLC. As observed clinically for other tyrosine kinase inhibitors, mutations in ALK and ROS1 that confer acquired resistance have been observed for crizotinib as well as second-generation ALK inhibitors, such as ceritinib, alectinib, and brigatinib (Gainor et al. Molecular Mechanisms of Resistance to First- and Second-Generation ALK Inhibitors in ALK-Rearranged Lung Cancer, Cancer Discov. 2016; 6 (10): 1118-33; Awad et al., Acquired Resistance to Crizotinib from a Mutation in CD74-ROS1, N Engl J Med 2013; 368:2395-2401). Thus, there remains a need to identify compounds having novel activity profiles against wild-type and mutant forms of ALK and ROS1.

The present invention provides a novel crystalline form of lorlatinib free base, hydrate Form 24, having desirable properties relative to anhydrous lorlatinib free base (Form 7) and lorlatinib acetic acid solvate (Form 3), such as improved physical stability in aqueous-based formulations (e.g., topical formulations), and improved properties relative to lorlatinib hydrate (Form 1), which had unfavorable properties such as high hygroscopicity and multiple thermal transitions.

BRIEF SUMMARY OF THE INVENTION

In one aspect, the invention provides a novel crystalline form of lorlatinib free base hydrate (Form 24). Form 24 is characterized by one or more of the following methods: (1) powder X-ray diffraction (PXRD) (2θ); (2) $^{13}$C solid state NMR spectroscopy (ppm); or (3) $^{19}$F solid state NMR spectroscopy (ppm).

Figure 1:
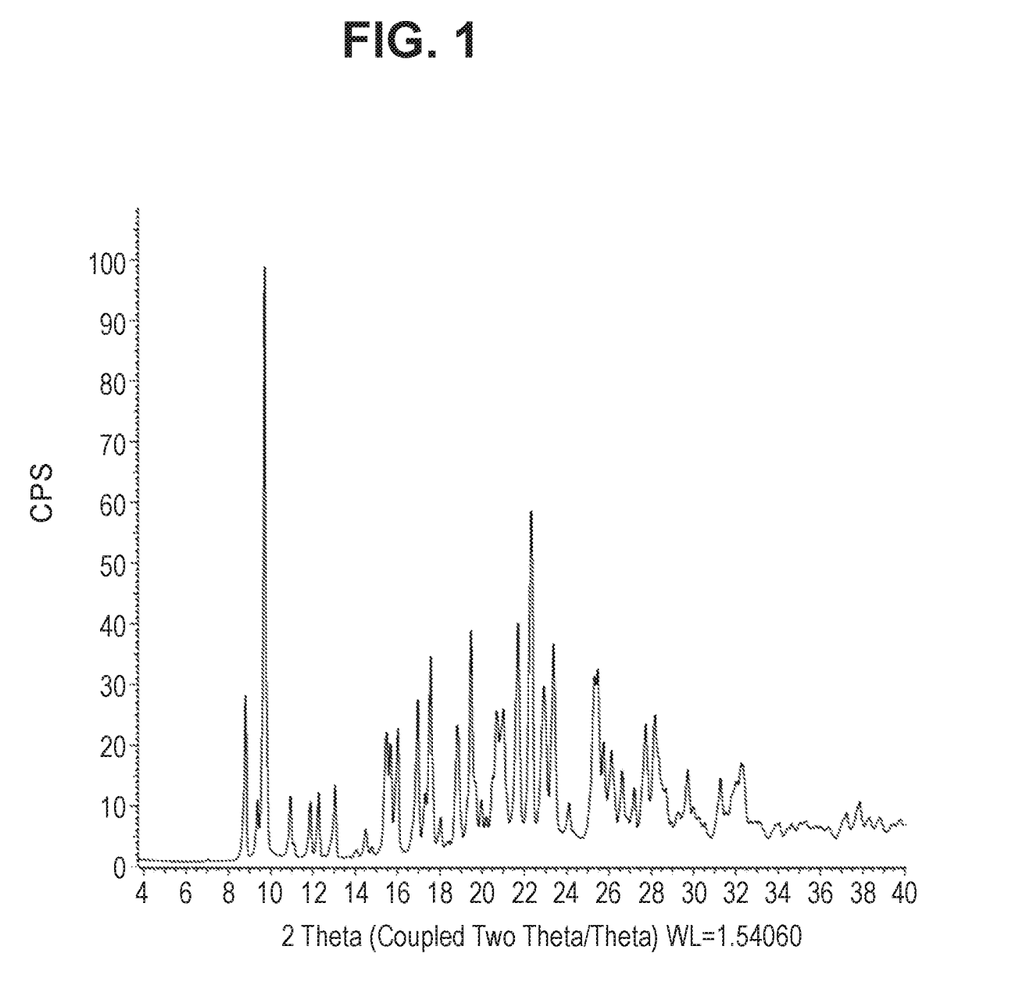
FIG. 1. PXRD pattern of lorlatinib free base hydrate (Form 24).
Figure 2:
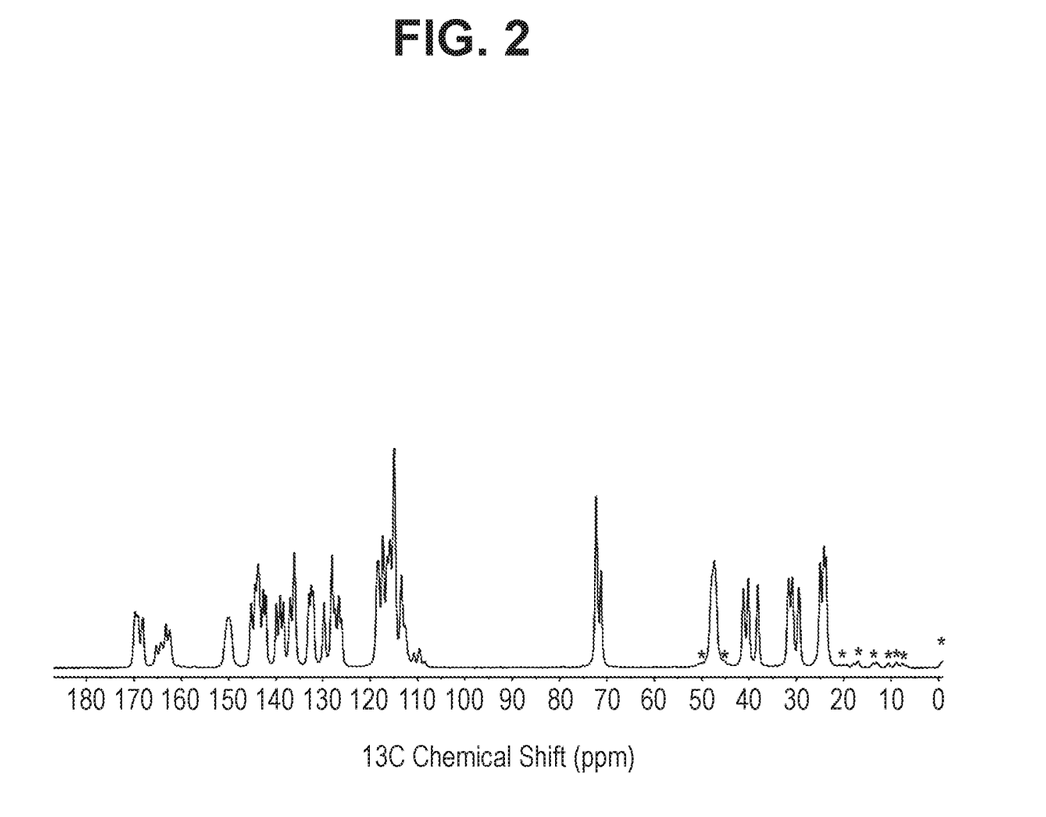
FIG. 2. $^{13}$C Carbon CPMAS spectrum of lorlatinib free base hydrate (Form 24). Peaks marked by hash marks are spinning sidebands.
Figure 3:
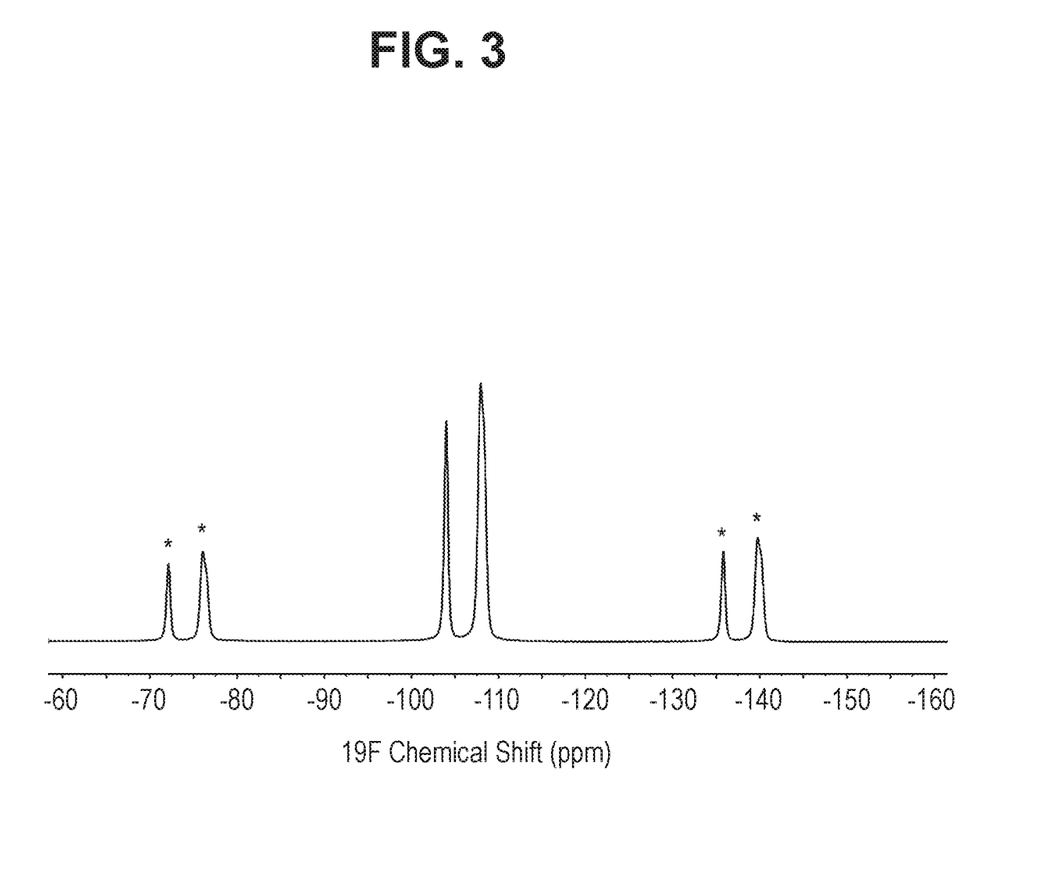
FIG. 3. $^{19}$Fluorine MAS spectrum of lorlatinib free base hydrate (Form 24). Peaks marked by hash marks are spinning sidebands.

In a first aspect, the invention provides lorlatinib free base hydrate (Form 24), which is characterized by having:

(1) a powder X-ray diffraction (PXRD) pattern (2θ) comprising: (a) one, two, three, four, five, or more than five peaks selected from the group consisting of the peaks in Table 1 in °2θ±0.2 °2θ; (b) one, two, three, four or five peaks selected from the group consisting of the characteristic peaks in Table 1 in °2θ±0.2 °2θ; or (c) peaks at 2θ values essentially the same as shown in FIG. 1; or (2) a $^{13}$C solid state NMR spectrum (ppm) comprising: (a) one, two, three, four, five, or more than five resonance (ppm) values selected from the group consisting of the values in Table 2 in ppm±0.2 ppm; (b) one, two, three, four or five resonance (ppm) values selected from the group consisting of the characteristic values in Table 2 in ppm±0.2 ppm; or (c) resonance (ppm) values essentially the same as shown in FIG. 2; or (3) a $^{19}$F solid state NMR spectrum (ppm) comprising: (a) one, two or three resonance (ppm) values selected from the group consisting of the values in Table 3 in ppm±0.2 ppm; or (b) resonance (ppm) values essentially the same as shown in FIG. 3;

or a combination of any two or three of the foregoing embodiments (1)(a)-(c), (2)(a)-(c) or (3)(a)-(b), provided they are not inconsistent with each other.

In another aspect, the invention further provides a pharmaceutical composition comprising lorlatinib free base hydrate (Form 24), according to any of the aspects or embodiments described herein, and a pharmaceutically acceptable carrier or excipient.

The crystalline form of lorlatinib free base hydrate (Form 24), according to any of the aspects or embodiments described herein, may be used for the treatment of abnormal cell growth, such as cancer, in a mammal.

In one aspect, the invention provides a method of treating abnormal cell growth in a mammal, including a human, comprising administering to the mammal a therapeutically effective amount of the crystalline form of lorlatinib free base hydrate (Form 24).

In another aspect, the invention provides the crystalline form of lorlatinib free base hydrate (Form 24) for use as a medicament, particularly for use in the treatment of abnormal cell growth in a mammal, including a human.

In another aspect, the invention provides a method of treating abnormal cell growth in a mammal, comprising administering to the mammal a therapeutically effective amount of a pharmaceutical composition comprising the crystalline form of lorlatinib free base hydrate (Form 24), according to any of the aspects or embodiments described herein.

In another aspect, the invention provides use of the crystalline form of lorlatinib free base hydrate (Form 24), or a pharmaceutical composition comprising such Form 24, according to any of the aspects or embodiments described herein, in a method of treating abnormal cell growth in a mammal.

In yet another aspect, the invention provides use of the crystalline form of lorlatinib free base hydrate (Form 24), according to any of the aspects or embodiments described herein, in the manufacture of a medicament for the treatment of abnormal cell growth in a mammal.

In another aspect, the invention provides the crystalline form of lorlatinib free base hydrate (Form 24) according to any of the aspects or embodiments described herein, or a pharmaceutical composition comprising such Form 24, for use as a medicament.

In another aspect, the invention provides the crystalline form of lorlatinib free base hydrate (Form 24) according to any of the aspects or embodiments described herein, or a pharmaceutical composition comprising such Form 24, for use in the treatment of abnormal cell growth in a mammal.

In frequent embodiments of each of the aspects described herein, the abnormal cell growth is cancer. In some such embodiments, the abnormal cell growth is cancer mediated by ALK or ROS1. In some embodiments, the abnormal cell growth is cancer mediated by ALK. In other embodiments, the abnormal cell growth is cancer mediated by ROS1. In further embodiments, the abnormal cell growth is cancer mediated by at least one genetically altered tyrosine kinase, such as a genetically altered ALK or a genetically altered ROS1 kinase. In some such embodiments, the cancer is selected from the group consisting of non-small cell lung cancer (NSCLC), neuroblastoma, anaplastic large cell lymphoma (ALCL) and gastric cancer. In specific embodiments, the cancer is non-small cell lung cancer (NSCLC). In particular embodiments, the cancer is NSCLC mediated by ALK or ROS1, and more particularly, NSCLC mediated by a genetically altered ALK or a genetically altered ROS1.

DETAILED DESCRIPTION OF THE INVENTION

The present invention may be understood more readily by reference to the following detailed description of the embodiments of the invention and the Examples included herein. It is to be understood that the terminology used herein is for the purpose of describing specific embodiments only and is not intended to be limiting. It is further to be understood that unless specifically defined herein, the terminology used herein is to be given its traditional meaning as known in the relevant art.

As used herein, the singular form "a", "an", and "the" include plural references unless indicated otherwise. For example, "a" substituent includes one or more substituents.

The term "about" means having a value falling within an accepted standard of error of the mean, when considered by one of ordinary skill in the art.

As used herein, the term "essentially the same" means that variability typical for a particular method is taken into account. For example, with reference to X-ray diffraction peak positions, the term "essentially the same" means that typical variability in peak position and intensity are taken into account. One skilled in the art will appreciate that the peak positions (2θ) will show some variability, typically as much as ±0.2° 2θ. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measures only. Similarly, $^{13}$C and $^{19}$F solid state NMR spectrum (ppm) show variability, typically as much as ±0.2 ppm.

The term "crystalline" as used herein, means having a regularly repeating arrangement of molecules or external face planes. Crystalline forms may differ with respect to thermodynamic stability, physical parameters, x-ray structure and preparation processes.

The term "amorphous" refers to a disordered solid state.

The term "solvate" as used herein, means having, in a lattice, a stoichiometric or non-stoichiometric amount of a solvent such as water, acetic add, methanol, etc., or mixtures thereof, bound by non-covalent intermolecular forces.

The term "hydrate" may be used specifically to describe a solvate comprising water.

The term "channel hydrate" may be used to describe stoichiometric or non-stoichiometric hydrates having water filled one dimensional channels or two dimensional planes in the crystal structure. The amount of water in the crystal lattice of a non-stoichiometric hydrate may vary with the partial pressure of water in the surrounding atmosphere and with temperature.

The invention described herein may be suitably practiced in the absence of any element(s) not specifically disclosed herein. Thus, for example, in each instance herein any of the terms "comprising", "consisting essentially of", and "consisting of" may be replaced with either of the other two terms.

In one aspect, the invention provides lorlatinib free base hydrate (Form 24). As disclosed herein, Form 24 is a crystalline form of lorlatinib free base hydrate having improved physical stability in aqueous-based formulations, for example topical formulations. The methods described herein provide lorlatinib free base hydrate (Form 24) which is substantially pure and substantially free of alternative forms, including the anhydrous free base (Form 7) and the solvated forms (Forms 1, 2 and 3) disclosed previously. In preferred embodiments of each of the aspects described herein, lorlatinib free base hydrate (Form 24) is substantially pure.

As used herein, the term "substantially pure" means that the crystalline form contains at least 90%, preferably at least 95%, more preferably at least 97%, and most preferably at least 99% by weight of the indicated crystalline form (e.g., Form 24). Alternatively, it will be understood that "substantially pure" means that the crystalline form contains less than 10%, preferably less than 5%, more preferably less than 3%, and most preferably less than 1% by weight of impurities, including other polymorphic, solvated or amorphous forms.

As described herein, Form 24 was characterized by PXRD, and $^{13}$C and $^{19}$F solid state NMR spectroscopy. Such crystalline forms may be further characterized by additional techniques, such as Raman spectroscopy, Fourier-Transform InfraRed Spectroscopy (FTIR), Differential Scanning Calorimetry (DSC), Thermogravimetric Analysis (TGA) or Differential Thermal Analysis (DTA). Dynamic vapor sorption (DVS) methods may be used to explore the sorption/desorption behavior of Form 24 under various conditions of temperature and relative humidity (RH).

In some embodiments of each of the aspects of the invention, lorlatinib free base hydrate (Form 24) is characterized by its powder X-ray diffraction (PXRD) pattern. In other embodiments of each of the aspects of the invention, lorlatinib free base hydrate (Form 24) is characterized by its $^{13}$C solid state NMR spectrum. In still other embodiments of each of the aspects of the invention, lorlatinib free base hydrate (Form 24) is characterized by its $^{19}$F solid state NMR spectrum. Lorlatinib free base hydrate (Form 24) may be uniquely identified relative to lorlatinib solid forms described previously (e.g., Forms 1, 2, 3 and 7) by the characteristic peaks identified herein, using each of these techniques alone or in combination.

In further embodiments, lorlatinib free base hydrate (Form 24) is characterized by a combination of two or three of these methods. Exemplary combinations including two or more of the following are provided herein: powder X-ray diffraction (PXRD) pattern (2θ); $^{13}$C solid state NMR spectrum (ppm); or $^{19}$F solid state NMR spectrum (ppm). It will be understood that other combinations of techniques may be used to uniquely characterize lorlatinib free base hydrate (Form 24) disclosed herein.

In one embodiment, lorlatinib free base hydrate (Form 24) has a PXRD pattern comprising one or more peaks at 2θ values selected from the group consisting of: 8.8, 9.7, 10.9, 17.6 and 18.8 °2θ±0.2 °2θ. In another embodiment, lorlatinib free base hydrate (Form 24) has a PXRD pattern comprising two or more peaks at 2θ values selected from the group consisting of: 8.8, 9.7, 10.9, 17.6 and 18.8 °2θ±0.2 °2θ. In another embodiment, lorlatinib free base hydrate (Form 24) has a PXRD pattern comprising three or more peaks at 2θ values selected from the group consisting of: 8.8, 9.7, 10.9, 17.6 and 18.8 °2θ±0.2 °2θ.

In another embodiment, Form 24 has a PXRD pattern comprising peaks at 2θ values of: 8.8, 17.6 and 18.8 °2θ±0.2 °2θ. In some such embodiments, Form 24 has a PXRD pattern further comprising a peak at the 2θ value of: 9.7 °2θ±0.2 °2θ. In other such embodiments, Form 24 has a PXRD pattern further comprising a peak at the 2θ value of: 10.9° 2θ±0.2 °2θ.

In another embodiment, lorlatinib free base hydrate (Form 24) has a PXRD pattern comprising a peak at a 2θ value of: 8.8° 2θ±0.2 °2θ. In another embodiment, Form 24 has a PXRD pattern comprising a peak at a 2θ value of: 9.7 °2θ±0.2 °2θ. In another embodiment, Form 24 has a PXRD pattern comprising a peak at a 2θ value of: 10.9° 2θ±0.2 °2θ. In another embodiment, Form 24 has a PXRD pattern comprising a peak at a 2θ value of: 17.6° 2θ±0.2 °2θ. In another embodiment, Form 24 has a PXRD pattern comprising a peak at a 2θ value of: 18.8 °2θ±0.2 °2θ.

In another embodiment, lorlatinib free base hydrate (Form 24) has a PXRD pattern comprising peaks at 2θ values of: 8.8, 9.7, 17.6 and 18.8 °2θ±0.2 °2θ. In another embodiment, lorlatinib free base hydrate (Form 24) has a PXRD pattern comprising peaks at 2θ values of: 8.8, 10.9, 17.6 and 18.8 °2θ±0.2 °2θ. In yet another embodiment, lorlatinib free base hydrate (Form 24) has a PXRD pattern comprising peaks at 2θ values of: 8.8, 9.7, 10.9, 17.6 and 18.8 °2θ±0.2 °2θ. In some such embodiments, the PXRD pattern further comprises one or more additional peaks at 2θ values selected from the group consisting of the peaks in Table 1.

In specific embodiments, lorlatinib free base hydrate (Form 24) has a PXRD pattern comprising: (a) one, two, three, four, five, or more than five peaks selected from the group consisting of the peaks in Table 1 in °2θ±0.2 °2θ; (b) one, two, three, four or five peaks selected from the group consisting of the characteristic peaks in Table 1 in °2θ±0.2 °2θ; or (c) peaks at 2θ values essentially the same as shown in FIG. 1.

In one embodiment, lorlatinib free base hydrate (Form 24) has a $^{13}$C solid state NMR spectrum comprising one or more resonance (ppm) values selected from the group consisting of: 40.2, 41.2, 128.1, 136.2 and 145.3 ppm±0.2 ppm. In another embodiment, lorlatinib free base hydrate (Form 24) has a $^{13}$C solid state NMR spectrum comprising two or more resonance (ppm) values selected from the group consisting of: 40.2, 41.2, 128.1, 136.2 and 145.3 ppm±0.2 ppm. In another embodiment, lorlatinib free base hydrate (Form 24) has a $^{13}$C solid state NMR spectrum comprising three or more resonance (ppm) values selected from the group consisting of: 40.2, 41.2, 128.1, 136.2 and 145.3 ppm±0.2 ppm.

In some embodiments, lorlatinib free base hydrate (Form 24) has a $^{13}$C solid state NMR spectrum comprising the resonance (ppm) values of: 40.2, 41.2 and 136.2 ppm±0.2 ppm. In some such embodiments, Form 24 has a $^{13}$C solid state NMR spectrum further comprising the resonance (ppm) value of: 128.1 ppm±0.2 ppm. In other such embodiments, Form 24 has a $^{13}$C solid state NMR spectrum further comprising the resonance (ppm) value of: 145.3 ppm±0.2 ppm. In still other such embodiments, Form 24 has a $^{13}$C solid state NMR spectrum further comprising the resonance (ppm) values of: 128.1 and 145.3 ppm±0.2 ppm.

In another embodiment, Form 24 has a $^{13}$C solid state NMR spectrum comprising the resonance (ppm) values of: 40.2, 41.2, 128.1 and 136.2 ppm±0.2 ppm. In another embodiment, Form 24 has a $^{13}$C solid state NMR spectrum comprising the resonance (ppm) values of: 40.2, 41.2, 136.2 and 145.3 ppm±0.2 ppm. In another embodiment, Form 24 has a $^{13}$C solid state NMR spectrum comprising the resonance (ppm) values of: 40.2, 41.2, 128.1, 136.2 and 145.3 ppm±0.2 ppm.

In specific embodiments, lorlatinib free base hydrate (Form 24) has a $^{13}$C solid state NMR spectrum (ppm) comprising: (a) one, two, three, four, five, or more than five resonance (ppm) values selected from the group consisting of the values in Table 2 in ppm±0.2 ppm; (b) one, two, three, four or five resonance (ppm) values selected from the group consisting of the characteristic values in Table 2 in ppm±0.2 ppm; or (c) resonance (ppm) values essentially the same as shown in FIG. 2.

In one embodiment, lorlatinib free base hydrate (Form 24) has a $^{19}$F solid state NMR spectrum comprising a resonance (ppm) value of: −104.0 ppm±0.2 ppm.

In another embodiment, Form 24 has a $^{19}$F solid state NMR spectrum (ppm) comprising: (a) one, two or three resonance (ppm) values selected from the group consisting of the values in Table 3 in ppm±0.2 ppm; or (b) resonance (ppm) values essentially the same as shown in FIG. 3.

In further embodiments, lorlatinib free base hydrate (Form 24) is characterized by a combination of two or three of the embodiments described above that are not inconsistent with each other.

Exemplary embodiments that may be used to uniquely characterize lorlatinib free base hydrate (Form 24) are provided below.

In one embodiment, lorlatinib free base hydrate (Form 24) has a powder X-ray diffraction pattern comprising peaks at 2θ values of: 8.8, 17.6 and 18.8 °2θ±0.2 °2θ.

In another embodiment, lorlatinib free base hydrate (Form 24) has a powder X-ray diffraction pattern comprising peaks at 2θ values of: 8.8, 9.7, 17.6 and 18.8 °2θ±0.2 °2θ.

In another embodiment, lorlatinib free base hydrate (Form 24) has a powder X-ray diffraction pattern comprising peaks at 2θ value of: 8.8, 10.9, 17.6 and 18.8 °2θ±0.2 °2θ.

In another embodiment, lorlatinib free base hydrate (Form 24) has a powder X-ray diffraction pattern comprising peaks at 2θ value of: 8.8, 9.7, 10.9, 17.6 and 18.8 °2θ±0.2 °2θ.

In still another embodiment, lorlatinib free base hydrate (Form 24) has a $^{19}$F solid state NMR spectrum comprising the resonance (ppm) value of: −104.0 ppm±0.2 ppm.

In another embodiment, lorlatinib free base hydrate (Form 24) has a $^{13}$C solid state NMR spectrum comprising resonance (ppm) values of: 40.2, 41.2 and 136.2 ppm±0.2 ppm.

In another embodiment, lorlatinib free base hydrate (Form 24) has a $^{13}$C solid state NMR spectrum comprising resonance (ppm) values of: 40.2, 41.2, 128.1 and 136.2 ppm±0.2 ppm.

In yet embodiment, lorlatinib free base hydrate (Form 24) has a $^{13}$C solid state NMR spectrum comprising resonance (ppm) values of: 40.2, 41.2, 136.2 and 145.3 ppm±0.2 ppm.

In still another embodiment, lorlatinib free base hydrate (Form 24) has a $^{13}$C solid state NMR spectrum comprising resonance (ppm) values of: 40.2, 41.2, 128.1, 136.2 and 145.3 ppm±0.2 ppm.

In a further embodiment, lorlatinib free base hydrate (Form 24) has: (a) a powder X-ray diffraction pattern comprising peaks at 2θ values of: 8.8, 17.6 and 18.8 °2θ±0.2 °2θ; and (b) a $^{13}$C solid state NMR spectrum comprising resonance (ppm) values of: 40.2, 41.2 and 136.2 ppm±0.2 ppm.

In a further embodiment, lorlatinib free base hydrate (Form 24) has: (a) a powder X-ray diffraction pattern comprising peaks at 2θ values of: 8.8, 17.6 and 18.8 °2θ±0.2 °2θ; and (b) a $^{19}$F solid state NMR spectrum comprising the resonance (ppm) value of: −104.0 ppm±0.2 ppm.

In a further embodiment, lorlatinib free base hydrate (Form 24) has: (a) a $^{13}$C solid state NMR spectrum comprising resonance (ppm) values of: 40.2, 41.2 and 136.2 ppm±0.2 ppm; and (b) a $^{19}$F solid state NMR spectrum comprising the resonance (ppm) value of: −104.0 ppm±0.2 ppm.

In another aspect, the invention provides a pharmaceutical composition comprising lorlatinib free base hydrate (Form 24) characterized according to any of the embodiments described herein, and a pharmaceutically acceptable carrier or excipient.

In another aspect, the invention provides method of treating abnormal cell growth in a mammal, preferably a human, comprising administering to the mammal a therapeutically effective amount of a pharmaceutical composition of the invention.

The term "therapeutically effective amount" as used herein refers to that amount of a compound being administered which will relieve to some extent one or more of the symptoms of the disorder being treated. In reference to the treatment of cancer, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth or tumor invasiveness, and/or (4) relieving to some extent (or, preferably, eliminating) one or more signs or symptoms associated with the cancer.

As used herein, "mammal" refers to a human or animal subject. In certain preferred embodiments, the mammal is a human.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject.

"Abnormal cell growth", as used herein, unless otherwise indicated, refers to cell growth that is independent of normal regulatory mechanisms (e.g., loss of contact inhibition). Abnormal cell growth may be benign (not cancerous), or malignant (cancerous). In frequent embodiments of the methods provided herein, the abnormal cell growth is cancer.

As used herein "cancer" refers to any malignant and/or invasive growth or tumor caused by abnormal cell growth. The term "cancer" includes but is not limited to a primary cancer that originates at a specific site in the body, a metastatic cancer that has spread from the place in which it started to other parts of the body, a recurrence from the original primary cancer after remission, and a second primary cancer that is a new primary cancer in a person with a history of previous cancer of different type from latter one.

In some embodiments, the abnormal cell growth is cancer mediated by an anaplastic lymphoma kinase (ALK). In some such embodiments, the ALK is a genetically altered ALK. In other embodiments, the abnormal cell growth is cancer mediated by ROS1 kinase. In some such embodiments, the ROS1 kinase is a genetically altered ROS1 kinase. In frequent embodiments, the abnormal cell growth is cancer, in particular NSCLC. In some such embodiments, the NSCLC is mediated by ALK or ROS1. In specific embodiments, the cancer is NSCLC is mediated by genetically altered ALK or genetically altered ROS1.

The moisture sorption/desorption behavior for lorlatinib free base hydrate (Form 24) revealed that this structure gradually sorbs/desorbs different levels of water as a result of a change of relative humidity. Such a moisture profile is typical of a channel (variable) hydrate. Analysis indicates that both sorption and desorption processes for all humidity levels did not reach equilibrium easily, as the structure sorbs and desorbs water very slowly and gradually. The observed behavior was found to be reproducible for different batches of Form 24. The water levels changes between a dry and wet state of Form 24 were examined as well. The change of mass for Form 24 between these two states was below 1%. Although the structure gradually increased in weight over time when exposed to high relative humidity, the stoichiometric water levels for mono or hemi-hydrate forms were not achieved. Form 24 may in some instances be referred as a non-stoichiometric hydrate or a non-stoichiometric channel hydrate.

Pharmaceutical compositions of the present invention may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see Remington's Pharmaceutical Sciences, Mack Publishing Company, Easter, Pa., 15th Edition (1975).

EXAMPLES

The examples and preparations provided below further illustrate and exemplify particular aspects and embodiments of the invention. It is to be understood that the scope of the present invention is not limited by the scope of the following examples.

General Method 1. Powder X-ray Diffraction (PXRD)

Figure 4:
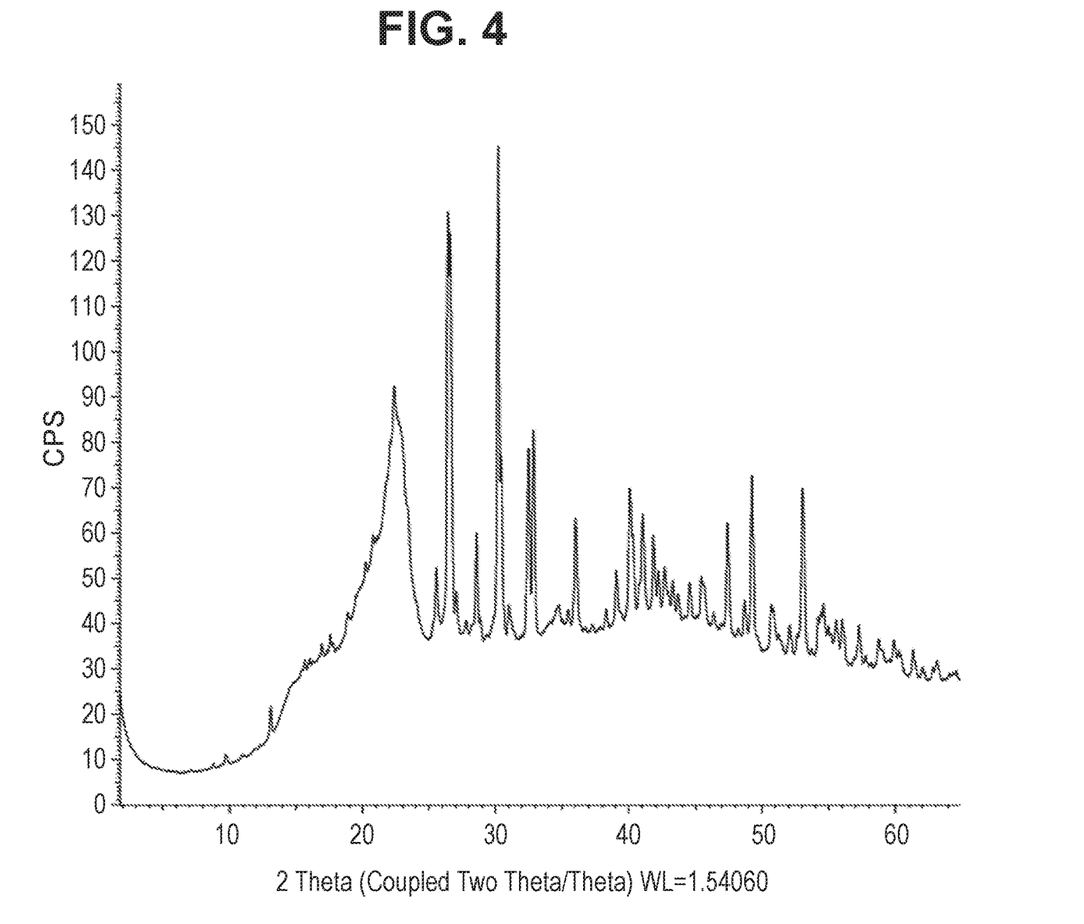
FIG. 4. PXRD pattern of uncoated prototype tablet of lorlatinib free base hydrate (Form 24).

The PXRD data in FIGS. 1 and 4 were collected according to the following general protocol.
Instrument Method PXRD patterns were collected on a Bruker-AXS Ltd. D4 powder X-ray diffractometer fitted with an automatic sample changer, a theta-theta goniometer, automatic beam divergence slit, and a PSD Vantec-1 detector. The X-ray tube voltage and amperage were set to 40 kV and 40 mA respectively. The diffractometer was aligned and a calibration check performed using a corundum reference material on the day of data collection. Data was collected at the Cu K-alpha wavelength using a step size of 0.018 degrees and scan time and 11.3 hours scanning from 2.0 to 65.0 degrees 2-theta. The sample powders were prepared by placing the powder in low background cavity holder. The sample powder was pressed by a glass slide to ensure that a proper sample height was achieved. The prototype 25 mg uncoated tablet (lot 00708989-0037-3) sample was cleaved to unsure appropriate height and also smooth and even tablet surface. It was mounted on to a set specimen holder, secured with blue tack and covered with Kapton film. Data were collected using Bruker DIFFRAC software and analysis was performed by DIFFRAC EVA software (Version 3.1).
Peak Picking Method The PXRD patterns collected were imported into Bruker DIFFRAC EVA software. The peak selection carried out manually was carefully checked to ensure that all peaks had been captured and all peak positions had been accurately assigned. The peak list for peaks with 2-theta lower than 25 2-theta degrees was extracted from the Bruker software into Microsoft Excel and peak intensities were normalized relative to highest intensity peak equaling 100%. A typical error of ±0.2° 2-theta in peak positions applies to this data. The minor error associated with this measurement can occur as a result of a variety of factors including: (a) sample preparation (e.g., sample height), (b) instrument, (c) calibration, (d) operator (including those errors present when determining the peak locations), and (e) the nature of the material (e.g. preferred orientation and transparency errors). Therefore peaks are considered to have a typical associated error of ±0.2° 2-theta. When two peaks, in the list, are considered to overlap (±0.2° 2-theta) the less intense peak has been removed from the listing. Peaks existing as shoulders, on a higher intensity adjacent peak, have also been removed from the peak list. While the shoulders may be >0.2° 2-theta from the position of the adjacent peak, they are not considered as discernible from the adjacent peak. In order to obtain the absolute peak positions, the powder pattern should be aligned against a reference. This could either be the simulated powder pattern from the crystal structure of the same form solved at room temperature, or an internal standard e.g. silica.

The PXRD profile for the active pharmaceutical ingredient (API) is provided in FIG. 1 and selected peak positions are provided in Table 1. The PXRD profile for a 25 mg uncoated prototype tablet is provided in FIG. 4.

General Method 2. Solid State NMR (ssNMR) Spectroscopy

The carbon CPMAS and fluorine MAS ssNMR data in FIGS. 2, 3, 5 and 6 were collected according to the following general protocol.
Instrument Method

Solid state NMR (ssNMR) analysis on Form 24 was conducted at ambient temperature on a Bruker-BioSpin CPMAS probe positioned into a Bruker-BioSpin Avance III 500 MHz ($^1$H frequency) NMR spectrometer. The packed rotor was oriented at the magic angle and spun at 15.00 kHz. The carbon ssNMR spectrum was collected using a proton decoupled cross-polarization magic angle spinning experiment. A phase modulated proton decoupling field of 80-90 kHz was applied during spectral acquisition. The cross-polarization contact time was set to 2 ms and the recycle delay to 5 seconds. The number of scans was adjusted to obtain an adequate signal to noise ratio. The carbon spectrum was referenced using an external standard of crystalline adamantane, setting its upfield resonance to 29.5 ppm (as determined from neat TMS). The fluorine ssNMR spectrum was collected using a proton decoupled direct polarization magic angle spinning experiment. A phase modulated proton decoupling field of 80-90 kHz was applied during spectral acquisition. The recycle delay was set to 50 seconds. The number of scans was adjusted to obtain an adequate signal to noise ratio. The direct polarization fluorine spectrum was referenced using an external standard of 50/50 volume/volume of trifluoroacetic acid and water, setting its resonance to −76.54 ppm.
Peak Picking Method Automatic peak picking was performed using Bruker-BioSpin TopSpin version 3.2 software. Generally, a threshold value of 5% relative intensity was used to preliminary select peaks. The output of the automated peak picking was visually checked to ensure validity and adjustments were manually made if necessary.

Although specific $^{13}$C and $^{19}$F solid state NMR peak values are reported herein, a range for these peak values exists due to differences in instruments, samples, and sample preparation. This is common practice in the art of solid state NMR because of the variation inherent in peak values. A typical variability for a $^{13}$C and $^{19}$F chemical shift x-axis value is on the order of plus or minus 0.2 ppm for a crystalline solid. The solid state NMR peak heights reported herein are relative intensities. The solid state NMR intensities can vary depending on the actual setup of the experimental parameters and the thermal history of the sample. The $^{13}$C solid state NMR spectrum of Form 24 API is provided in FIG. 2 and selected peak positions are provided in Table 2. $^{19}$F solid state NMR spectrum of Form 24 API is provided in FIG. 3 and selected peak positions are provided in Table 3. The $^{13}$C solid state NMR and $^{19}$F solid state NMR spectra for a 25 mg uncoated prototype tablet are provided in FIGS. 5 and 6.

Example 1

Preparation of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetra-decine-3-carbonitrile (lorlatinib) Free Base Hydrate (Form 24)

lorlatinib anhydrous free base
(Form 7)
PF-06463922
Form 12
[iPrOAc solvate]
1. toluene 80° C.
2. filtration lorlatinib free base hydrate
(Form 24)

A sample of anhydrous lorlatinib free base (Form 7) (1.52, 3.74 mmol) was added to a 15 mL vial. 4.80 mL of isopropyl acetate and 0.20 mL of water was added to give a water activity of approximately 0.35 and the mixture was stirred. The mixture was left to slurry for 24 hours on a roller mixer before the sample was isolated using vacuum filtration briefly to yield a damp product. A sample of the isolated product was analyzed using PXRD and was confirmed to be pure isopropyl acetate solvate of lorlatinib. The experiment gave a yield of 1.49777 g of damp isopropyl acetate solvate, which was not rigorously dried before taking into the next step. Four samples of the isopropyl acetate solvate, (306.88, 298.74, 298.31 and 303.50 mg, respectively) were added to four separate 2 mL vials. 700 μL of toluene was added to each of the vials along with magnetic stirrer bars and the vials were capped. The mixtures were heated to 80° C. and left to slurry for 72 hours before the slurry was isolated by centrifuge filtration. The samples were transferred to 0.22 μm nylon centrifuge filters and centrifuged at 13,200 rpm at 20° C. for 10 minutes. The isolated products were analyzed using PXRD and confirmed to be pure lorlatinib free base hydrate (Form 24).

Characterization of Lorlatinib Free Base Hydrate (Form 24)

PXRD Data

FIG. 1 shows PXRD data for lorlatinib free base hydrate (Form 24), collected according to General Method 1. A list of PXRD peaks at diffraction angles 2-Theta ° (° 2θ)±0.2

°2θ and their relative intensities is provided in Table 1. Characteristic PXRD peaks distinguishing Form 24 are indicated by an asterisk (*).

TABLE 1

PXRD Peak List for Form 24 (2-Theta °)

| Angle °2θ ± 0.2 °2θ | Intensity % |
|---|---|
| 8.8* | 28.1 |
| 9.7* | 100.0 |
| 10.9* | 10.6 |
| 11.9 | 9.6 |
| 12.3 | 11.1 |
| 13.1 | 12.1 |
| 15.7 | 18.4 |
| 16.0 | 21.0 |
| 17.0 | 27.0 |
| 17.6* | 32.7 |
| 18.8* | 20.7 |
| 19.5 | 37.2 |
| 20.7 | 22.6 |
| 21.0 | 23.0 |
| 21.7 | 37.3 |
| 22.3 | 56.1 |
| 22.9 | 26.5 |
| 23.4 | 33.5 | ssNMR data

FIG. 2 shows the carbon CPMAS spectrum of lorlatinib free base hydrate (Form 24), which was collected according to General Method 2. Chemical shifts are expressed in parts per million (ppm) and are referenced to external sample of solid phase adamantane at 29.5 ppm. A list of ssNMR $^{13}$C chemical shifts (ppm) for Form 24 is provided in Table 2 in ppm±0.2 ppm. Characteristic $^{13}$C ssNMR chemical shifts (ppm) distinguishing Form 24 are indicated by an asterisk (*).

TABLE 2

$^{13}$C ssNMR peak list for Form 24 (ppm)

| $^{13}$C Chemical Shifts [ppm ± 0.2 ppm] | Relative Intensity |
|---|---|
| 23.8 | 50 |
| 24.2 | 56 |
| 25.0 | 48 |
| 29.5 | 37 |
| 30.9 | 41 |
| 31.6 | 41 |
| 38.2 | 38 |
| 40.2* | 41 |
| 41.2* | 36 |
| 47.3 | 49 |
| 47.8 | 43 |
| 71.3 | 44 |
| 72.3 | 79 |
| 109.6 | 9 |
| 110.8 | 7 |
| 112.7 | 19 |
| 113.4 | 42 |
| 115.0 | 100 |
| 115.8 | 59 |
| 116.5 | 51 |
| 117.4 | 60 |
| 118.5 | 49 |
| 126.1 | 23 |
| 126.7 | 33 |
| 127.5 | 27 |
| 128.1* | 51 |
| 129.8 | 30 |
| 132.1 | 35 |
| 132.5 | 38 |

TABLE 2-continued $^{13}$C ssNMR peak list for Form 24 (ppm)

| $^{13}$C Chemical Shifts [ppm ± 0.2 ppm] | Relative Intensity |
|---|---|
| 133.0 | 34 |
| 136.2* | 53 |
| 137.0 | 32 |
| 138.5 | 30 |
| 139.2 | 33 |
| 139.9 | 29 |
| 142.2 | 34 |
| 142.8 | 36 |
| 143.8 | 47 |
| 144.4 | 38 |
| 145.3* | 29 |
| 149.9 | 23 |
| 150.2 | 23 |
| 162.5 | 17 |
| 163.3 | 20 |
| 164.3 | 12 |
| 165.3 | 10 |
| 168.2 | 23 |
| 169.2 | 24 |
| 169.7 | 26 |

FIG. 3 shows the fluorine MAS (ssNMR) spectrum of lorlatinib free base hydrate (Form 24), collected according to General Method 2. Chemical shifts are expressed in parts per million (ppm) referenced to an external sample of trifluoroacetic acid (50% V/V in $H_2O$) at −76.54 ppm.

The $^{19}$F ssNMR chemical shift (ppm) for Form 24 is provided in Table 3 in ppm±0.2 ppm. The characteristic ssNMR $^{19}$F chemical shifts (ppm) distinguishing Form 24 are indicated by an asterisk (*).

TABLE 3

$^{19}$F ssNMR Peak list for Form 24 (ppm)

| $^{19}$F Chemical Shifts [ppm ± 0.2 ppm] | Relative Intensity |
|---|---|
| −104.0* | 85 |
| −107.9 | 100 |
| −108.2 | 89 |

Example 2

Representative Drug Product Formulations of Lorlatinib Free Base hydrate (Form 24)

Prototype tablets comprising Form 24 of lorlatinib free base hydrate may be prepared using conventional excipients commonly used in tableted formulations.

Tablets typically contain from 1-30% of API on a w/w basis. Microcrystalline cellulose (e.g., 35-60% w/w), dibasic calcium phosphate anhydrous (DCP) (e.g., 10-35% w/w) may be used as tablet fillers. Other fillers, e.g., lactose monohydrate, may also be used in place of DCP. Sodium starch glycolate (e.g., 2-5% w/w) may be used as a disintegrant. Magnesium stearate (0.5-1.5% w/w) may be used as a lubricant.

Tablets may be manufactured using a dry granulation process prior to compression. In this process the crystalline material is blended with some proportion of the excipients falling within the typical ranges outlined above and the blend is dry granulated using a roller compactor. The granule may be milled as part of this process. The granules are blended with remainder of any of the excipients (e.g., magnesium stearate) prior to compression.

A representative tablet formulation of Form 24 is provided in Table 4.

TABLE 4

Example composition of prototype 25 mg uncoated DCP tablet, comprising 10% w/w of lorlatinib free base hydrate (Form 24)

| Component | Role | Mass % |
|---|---|---|
| lorlatinb free base hydrate Form 24 | Active ingredient | 10.00 |
| Cellulose Avicel PH 102 | Filler | 57.33 |
| Dibasic Calcium Phosphate DiCAFOS A12 | Filler | 28.67 |
| Sodium Starch Glycolate (Explotab) | Disintegrant | 3.00 |
| Magnesium Stearate | Lubricant | 1.00 |

Figure 5:
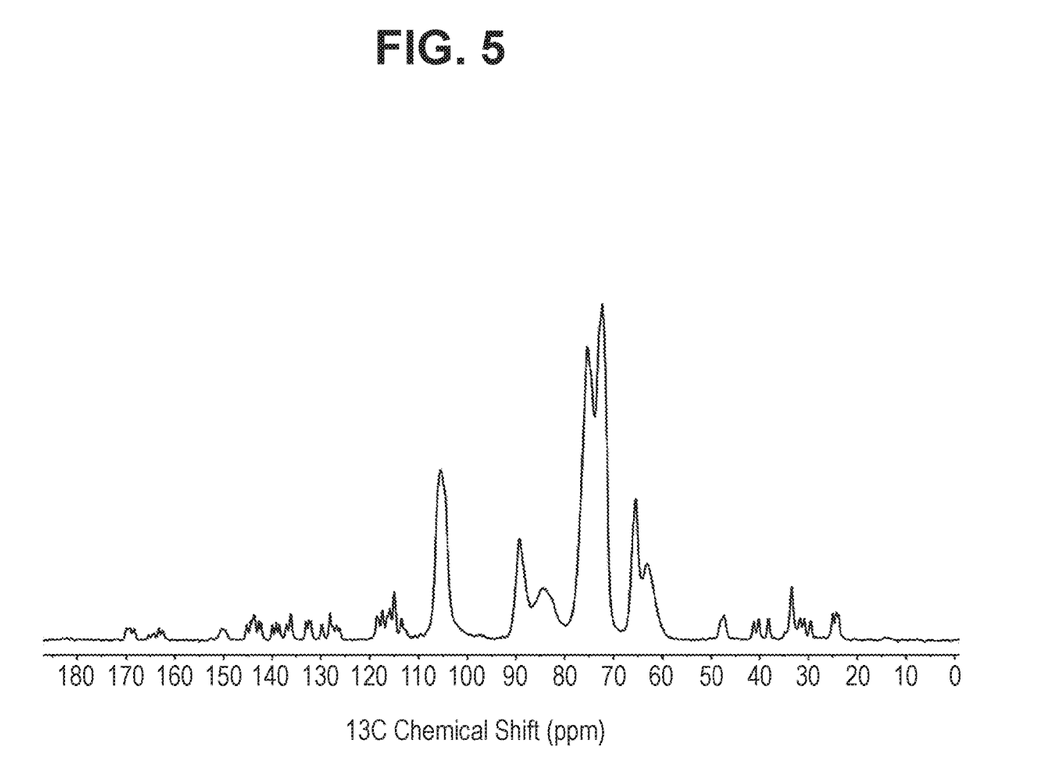
FIG. 5. $^{13}$Carbon CPMAS spectrum of uncoated prototype tablet of lorlatinib free base hydrate (Form 24).
Figure 6:
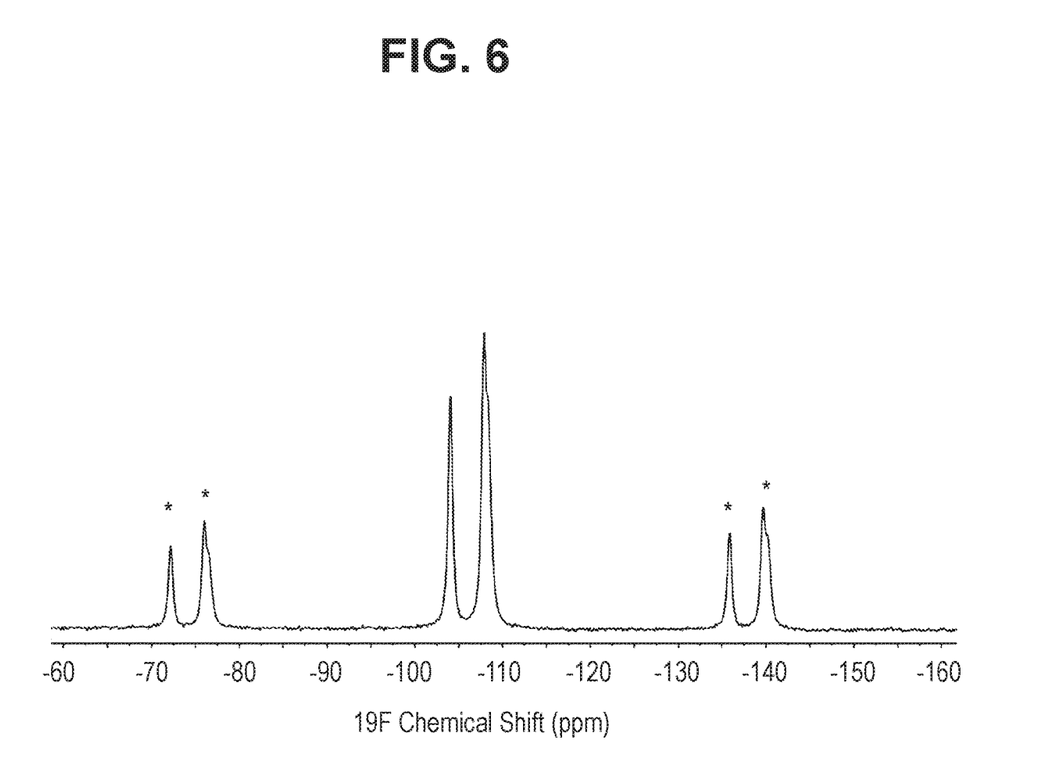
FIG. 6. Fluorine MAS spectrum of uncoated prototype tablet of lorlatinib free base hydrate (Form 24). Peaks marked by hash marks are spinning sidebands.

FIG. 4 shows the PXRD patterns of the prototype 25 mg uncoated tablet comprising lorlatinib free base hydrate (Form 24). FIGS. 5 and 6 show the $^{13}$C and $^{19}$F ssNMR spectra for the prototype 25 mg uncoated tablets, respectively.

Example 3

Water Sorption/Desorption Study for Lorlatinib Free Base Hydrate (Form 24)

A DVS method was employed to study the sorption/desorption behavior of Form 24.

Method: The method involved a standard sorption run from 0% RH to 90% RH, employing humidity rise at steps of 10% RH at 20° C., followed by a de-sorption run down to 0% RH and a second sorption/desorption cycle from 0% RH to 90% RH in 10% step change of RH at 20° C.

Results

Under the standard method, the material gradually increased the mass uptake of water at each humidity step from 0 to 90% RH. Specific mass increases due to water sorption at each relative humidity are provided in Table 5.

TABLE 5

Percent water absorbed in Form 24

| Targeted relative humidity (% RH) | % Water First Cycle | % Water Second Cycle |
|---|---|---|
| 0 | 0.00 | 0.00 |
| 10 | 0.06 | 0.06 |
| 20 | 0.13 | 0.13 |
| 30 | 0.19 | 0.20 |
| 40 | 0.27 | 0.27 |
| 50 | 0.34 | 0.35 |
| 60 | 0.43 | 0.44 |
| 70 | 0.52 | 0.54 |
| 80 | 0.64 | 0.65 |
| 90 | 0.78 | 0.78 |

A significant mass increase was observed at 90% RH compared to 0% RH. For both sorption cycles, the mass uptake at each humidity level exhibits an initial increase and then slowly continues to gradually increase with time. This may indicate that the rate of sorption and de-sorption is limited primarily by the rate of diffusion of water molecules through the pores of the crystal. Similar behavior was observed in the desorption cycles (i.e., a slight initial drop followed up by a gradual continuous drop). The de-sorption isotherms displayed very little hysteresis with respect to sorption isotherm, another feature typical of channel hydrates.

Since the increase of mass (sorption) and decrease of mass (de-sorption) gradually continued to change at each humidity level, it was hypothesized that equilibrium at each humidity level had not been reached.

For reference, stoichiometrically, a monohydrate corresponds to 4.2% change in mass and a 1:3 water: API stoichiometry corresponds to 1.4% change in mass. The measured change in mass for Form 24 was lower than the theoretically calculated stoichiometry, and therefore this structure can be considered a non-stoichiometric hydrate.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention.

We claim:

1. A crystalline form of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile (lorlatinib) free base hydrate, having a powder X-ray diffraction (PXRD) pattern comprising peaks at 2θ values of: 8.8, 9.7, 17.6 and 18.8 °2θ±0.2 °2θ.

2. The crystalline form of claim 1, having a PXRD pattern further comprising a peak at the 2θ value of: 10.9 °2θ±0.2 °2θ.

3. The crystalline form of claim 1, having a $^{13}$C solid state NMR spectrum comprising resonance (ppm) values of: 40.2, 41.2 and 136.2 ppm±0.2 ppm.

4. The crystalline form of claim 1, having a $^{19}$F solid state NMR spectrum comprising a resonance (ppm) value of: −104.0 ppm±0.2 ppm.

5. The crystalline form of lorlatinib free base hydrate of claim 1, for use as a medicament for treating cancer in a mammal, wherein the cancer is selected from the group consisting of ALK-positive non-small cell lung cancer (NSCLC) mediated by anaplastic lymphoma kinase (ALK) or c-ros oncogene 1 receptor tyrosine kinase (ROS1), ALK-positive anaplastic large cell lymphoma (ALCL), and ALK-positive neuroblastoma.

6. The crystalline form of lorlatinib free base hydrate of claim 1, for use in the treatment of cancer in a mammal, wherein the cancer is selected from the group consisting of ALK-positive non-small cell lung cancer (NSCLC) mediated by anaplastic lymphoma kinase (ALK) or c-ros oncogene 1 receptor tyrosine kinase (ROS1), ALK-positive anaplastic large cell lymphoma (ALCL), and ALK-positive neuroblastoma.

7. A pharmaceutical composition comprising the crystalline form of lorlatinib free base hydrate of claim 1, and a pharmaceutically acceptable carrier or excipient.

8. A method of treating cancer in a mammal comprising administering to the mammal a therapeutically effective amount of the crystalline form of lorlatinib free base hydrate of claim 1, wherein the cancer is selected from the group consisting of ALK-positive non-small cell lung cancer (NSCLC) mediated by anaplastic lymphoma kinase (ALK) or c-ros oncogene 1 receptor tyrosine kinase (ROS1), ALK-positive anaplastic large cell lymphoma (ALCL), and ALK-positive neuroblastoma.

9. A crystalline form of lorlatinib free base hydrate, having a $^{13}$C solid state NMR spectrum comprising two or more resonance (ppm) values of: 40.2, 41.2 and 136.2 ppm±0.2 ppm.

10. The crystalline form of claim 9, having a $^{13}$C solid state NMR spectrum further comprising the resonance (ppm) value of: 128.1 ppm±0.2 ppm.

11. The crystalline form of claim 9, having a $^{13}$C solid state NMR spectrum further comprising the resonance (ppm) value of: 145.3 ppm±0.2 ppm.

12. The crystalline form of claim 9, having a $^{19}$F solid state NMR spectrum comprising a resonance (ppm) value of: −104.0 ppm±0.2 ppm.

13. A crystalline form of lorlatinib free base hydrate, having a $^{19}$F solid state NMR spectrum comprising a resonance (ppm) value of: −104.0 ppm±0.2 ppm.

\* \* \* \* \*